US011938151B1

United States Patent
Ali et al.

(10) Patent No.: US 11,938,151 B1
(45) Date of Patent: Mar. 26, 2024

(54) **METHOD OF MAKING GOLD NANOPARTICLES CAPPED WITH *RESEDA ARABICA* EXTRACT AND TREATMENT METHOD USING THE SAME**

(71) Applicant: KING FAISAL UNIVERSITY, Al-Ahsa (SA)

(72) Inventors: Enas Mohamed Ali, Hofouf (SA); Basem Mohamed Abdallah, Hofouf (SA); Peramaiyan B. Rajendran, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/519,662

(22) Filed: Nov. 27, 2023

(51) Int. Cl.
*A61K 33/242* (2019.01)
*A61K 36/31* (2006.01)
*B82Y 5/00* (2011.01)

(52) U.S. Cl.
CPC ............ *A61K 33/242* (2019.01); *A61K 36/31* (2013.01); *B82Y 5/00* (2013.01)

(58) Field of Classification Search
CPC ......... A61K 33/242; A61K 36/31; B82Y 5/00
See application file for complete search history.

(56) References Cited

U.S. PATENT DOCUMENTS 9,358,310 B2 *  6/2016  Katti ................... A61K 31/353

FOREIGN PATENT DOCUMENTS

KR     20160047862 A     5/2016

OTHER PUBLICATIONS

H.R. El-Seedi. The traditional medical uses and cytotoxic activities of sixty-one Egyptian plants: Discovery of an active cardiac glycoside from Urginea maritimaJournal of Ethnopharmacology 145 (2013) 746-757). (Year: 2013).*

S. Chemat and R. Gharzouli. Ethnobotanical Study of Medicinal Flora in the North East of Algeria—An Empirical Knowledge in Djebel Zdimm (Setif), Journal of Materials Science and Engineering A 5 (1-2) (2015) 50-59. (Year: 2015).*

Boroumand, Majid Nasiri, et al. "Biosynthesis of silver nanoparticles using *Reseda luteola* L. and their antimicrobial activity." De Redactie 64 (2013): 123.

Boroumand, Majid Nasiri, et al. "Biocompatible stabilize silver nanoparticles and their antimicrobial activity." Advanced Science Letters 22.3 (2016): 616-621.

Ullah, Riaz, et al. "GC-MS analysis, heavy metals, biological, and toxicological evaluation of Reseda muricata and Marrubium vulgare methanol extracts." Evidence-Based Complementary and Alternative Medicine 2022 (2022).

Abdallah, Basem M., et al. "Therapeutic Potential of Green Synthesized Gold Nanoparticles Using Extract of Leptadenia hastata against Invasive Pulmonary Aspergillosis." Journal of Fungi 8.5 (2022): 442.

Aljabali, Alaa AA, et al. "Synthesis of gold nanoparticles using leaf extract of Ziziphus zizyphus and their antimicrobial activity." Nanomaterials 8.3 (2018): 174.

* cited by examiner

*Primary Examiner* — Michael P Cohen
(74) *Attorney, Agent, or Firm* — Nath, Goldberg & Meyer; Richard C. Litman

(57) ABSTRACT

In order to inhibit the growth of fungi, such as *Madurella mycetomatis*, gold nanoparticles are synthesized and capped with an extract of *Reseda arabica*. The gold nanoparticles capped with the extract of *Reseda arabica* are made by adding the extract of *Reseda arabica* to an aqueous sodium tetrachloroaurate ($NaAuCl_4$) solution to reduce the sodium tetrachloroaurate and form a suspension of gold nanoparticles capped with the extract of *Reseda arabica*. The extract of *Reseda arabica* acts as a reducing and stabilizing agent while also functionalizing the surfaces of the gold nanoparticles to cap the surfaces. The suspension may be boiled, followed by removal of the gold nanoparticles capped with the extract of *Reseda arabica* from the suspension. To treat a *Madurella mycetomatis* infection, an effective dose of the gold nanoparticles capped with *Reseda arabica* extract may be administered to a patient in need thereof.

1 Claim, No Drawings

METHOD OF MAKING GOLD NANOPARTICLES CAPPED WITH *RESEDA ARABICA* EXTRACT AND TREATMENT METHOD USING THE SAME

BACKGROUND

Field

The disclosure of the present patent application relates to antifungal agents, and particularly to a method of making gold nanoparticles capped with *Reseda arabica* extract, and further to a treatment method using the gold nanoparticles capped with *Reseda arabica* extract to inhibit growth of fungi, such as *Madurella mycetomatis*.

Description of Related Art

*Madurella mycetomatis* is a fungal strain which is responsible for eumycetoma infections in humans. Eumycetoma (also known as "Madura foot") is a persistent fungal infection of the skin and the tissues just under the skin, most commonly affecting the feet, although it can occur in hands and other body parts. Eumycetoma typically begins as a painless wet nodule, which may be present for years before ulceration, swelling, grainy discharge and weeping from sinuses and fistulae, followed by bone deformity. Treatment includes surgical removal of affected tissue and antifungal medicines. After treatment, recurrence is common, and amputation may be required.

*Madurella mycetomatis* is difficult to treat with traditional antifungal agents, thus alternative treatments are of great interest. Nanoparticles, both alone and used as carriers of antifungal agents, provide a promising avenue for treatment of *Madurella mycetomatis*. Presently, metallic nanoparticles are the most commonly used type of nanoparticles in antifungal therapy and act as both antifungal agents and drug nanocarriers. Metallic nanoparticles can eradicate microorganisms by disturbing their structure and functions. Specifically, the nanoparticles can disrupt the cell wall when positively charged ions of the nanoparticles bind to negatively charged components. This leads to the formation of pores in the cell wall, which allows cytoplasmic content to leak from the fungal cell, potentially leading to cell death.

Various metallic nanoparticles have been proposed for the targeted treatment of fungal infections, including gold (Au) nanoparticles and silver (Ag) nanoparticles. Gold and silver nanoparticles have received a great deal of interest in recent years for the treatment of various types of infections. Although the gold and silver nanoparticles are somewhat effective on their own, using the nanoparticles as both treatment agents and nanocarriers for additional antifungal agents is generally viewed as a highly promising treatment for most types of fungal infection. Since functionalizing or capping the nanoparticles with traditional antifungal agents would not be effective against *Madurella mycetomatis*, alternative agents, such as plant phytochemicals with antifungal properties, are of interest.

Thus, a method of making gold nanoparticles capped with *Reseda arabica* extract and a treatment method using the same solving the aforementioned problems are desired.

SUMMARY

In order to inhibit the growth of fungi, such as *Madurella mycetomatis*, as a non-limiting example, gold nanoparticles are synthesized and capped with an extract of *Reseda arabica*, a flowering plant in the Resedaceae family. The gold nanoparticles capped with the extract of *Reseda arabica* are made by adding the extract of *Reseda arabica* to an aqueous sodium tetrachloroaurate ($NaAuCl_4$) solution to reduce the sodium tetrachloroaurate and form a suspension of gold nanoparticles capped with the extract of *Reseda arabica*. The extract of *Reseda arabica* acts as a reducing and stabilizing agent while also functionalizing the surfaces of the gold nanoparticles to cap the surfaces. The suspension may be boiled, followed by removal of the gold nanoparticles capped with the extract of *Reseda arabica* from the suspension by centrifugation or the like.

In order to make the extract of *Reseda arabica*, aerial parts of *Reseda arabica* are macerated in water and butyric acid-free bitter ethanol. The macerated aerial parts of *Reseda arabica* are then filtered using filter paper or the like. The filtrates are collected, and the liquids are evaporated therefrom to form the extract of *Reseda arabica*. Evaporation may take place in a rotary evaporator or the like.

The gold nanoparticles capped with *Reseda arabica* extract exhibit strong antifungal activity. In order to treat a *Madurella mycetomatis* infection, an effective dose of the gold nanoparticles capped with *Reseda arabica* extract may be administered to a patient in need thereof.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a fungal infection.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In order to inhibit the growth of fungi, such as *Madurella mycetomatis*, as a non-limiting example, gold nanoparticles are synthesized and capped with an extract of *Reseda arabica*, a flowering plant in the Resedaceae family. The gold nanoparticles capped with the extract of *Reseda arabica* are made by adding the extract of *Reseda arabica* to an aqueous sodium tetrachloroaurate ($NaAuCl_4$) solution to reduce the sodium tetrachloroaurate and form a suspension of gold nanoparticles capped with the extract of *Reseda arabica*. The extract of *Reseda arabica* acts as a reducing and stabilizing agent while also functionalizing the surfaces of the gold nanoparticles to cap the surfaces. The suspension may be boiled, followed by removal of the gold nanoparticles capped with the extract of *Reseda arabica* from the suspension by centrifugation or the like.

In order to make the extract of *Reseda arabica*, aerial parts of *Reseda arabica* are macerated in water and butyric acid-free bitter ethanol. The macerated aerial parts of *Reseda arabica* are then filtered using filter paper or the like. The filtrates are collected and the liquids are evaporated therefrom to form the extract of *Reseda arabica*. Evaporation may take place in a rotary evaporator or the like.

The gold nanoparticles capped with *Reseda arabica* extract exhibit strong antifungal activity. In order to treat a *Madurella mycetomatis* infection, an effective dose of the gold nanoparticles capped with *Reseda arabica* extract may be administered to a patient in need thereof.

The gold nanoparticles capped with *Reseda arabica* extract exhibit strong antifungal activity. In order to treat a *Madurella mycetomatis* infection, an effective dose of the gold nanoparticles capped with *Reseda arabica* extract may be administered to a patient in need thereof.

The present nanoparticles can typically be administered at a therapeutically or pharmaceutically effective dosage, e.g., a dosage sufficient to provide treatment for a fungal infection. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present nanoparticles, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present nanoparticles for treatment of a fungal infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present nanoparticles can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

Example 1

Sodium tetrachloroaurate (III) dihydrate ($NaAuCl_4 \cdot 2H_2O$) was used to prepare a stock sodium tetrachloroaurate ($NaAuCl_4$) solution with an initial concentration of 1.0 mM in ultra-high purified water. The solution was boiled for 40 minutes and then left to cool to room temperature. The *Reseda arabica* extract was added to the pre-boiled sodium tetrachloroaurate (NaAuCl$_4$) solution in a 1:1 molar ratio. Specifically, 150.0 mL of 0.5% *Reseda arabica* extract (w/v) was added to 100.0 mL of 0.50 mM pre-boiled NaAuCl$_4$ solution in a 500.0 mL round-bottom flask. The mixture was boiled for 40 minutes until exhibiting an intense ruby red color, indicating the formation of gold nanoparticles capped with the extract of *Reseda arabica*.

Example 2

The aerial parts of *Reseda arabica* were macerated in water and butyric acid-free bitter ethanol at a 30:70 ratio (ethanol 70%). The resultant macerated aerial parts of *Reseda arabica* were filtered using filter paper and the liquids were evaporated therefrom under almost vacuum pressure at 50° C. using a rotary evaporator. The resultant concentrate was the extract of *Reseda arabica* used in Example 1 above, and was stored at −20° C. until use.

It is to be understood that the method of making gold nanoparticles capped with *Reseda arabica* extract and the treatment method using the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of treating a *Madurella mycetomatis* infection in a patient, comprising administering to a patient in need thereof an effective dose of gold nanoparticles capped with *Reseda arabica* extract.

\* \* \* \* \*